United States Patent
Le Beux

(10) Patent No.: US 6,188,782 B1
(45) Date of Patent: Feb. 13, 2001

(54) AUTOMATIC EDITING METHOD FOR A DIGITAL MEDICAL IMAGING UNIT

(75) Inventor: Jean-Claude Le Beux, Vincennes (FR)

(73) Assignee: Eastman Kodak Company, Rochester, NY (US)

( * ) Notice: Under 35 U.S.C. 154(b), the term of this patent shall be extended for 0 days.

(21) Appl. No.: 09/112,877

(22) Filed: Jul. 9, 1998

(30) Foreign Application Priority Data

Nov. 28, 1997  (FR) .................................................. 97 15337

(51) Int. Cl.$^7$ ........................................................ G06K 9/00
(52) U.S. Cl. ............................................................ 382/128
(58) Field of Search ..................................... 382/128, 132, 382/298, 305, 306; 345/438, 439; 378/62, 98; 358/1.2, 1.5, 1.12

(56) References Cited

U.S. PATENT DOCUMENTS

| | | |
|---|---|---|
| 5,027,274 | 6/1991 | Takayanagi . |
| 5,544,215 * | 8/1996 | Shroy et al. ................... 378/98.12 |
| 5,636,631 * | 6/1997 | Waitz et al. ........................ 600/437 |
| 5,734,915 * | 3/1998 | Roewer ................................ 707/512 |

FOREIGN PATENT DOCUMENTS 674187   9/1995 (EP) .

* cited by examiner

Primary Examiner—Joseph Mancuso
Assistant Examiner—F. E. Cooperrider
(74) Attorney, Agent, or Firm—Susan L. Parulski

(57) ABSTRACT

A digital medical imaging unit normally comprises: a station 10 for capturing information relating to a patient ID, a scanner 20 associated with a device 16, 18, 19 for capturing information relating to the medical examination to be processed for scanning first medical image media, an editing station 30 designed to send the digital images to be edited to a printer 50. The unit comprises an editing controller 40 which receives, before the processing of a first medical image medium, information relating to the editing and records an item of chronological information on the capture of the data so as to order chronologically the images delivered by the scanner in order to associate with each other the images of a series to be edited on one and the same page of the editing medium.

6 Claims, 5 Drawing Sheets

AUTOMATIC EDITING METHOD FOR A DIGITAL MEDICAL IMAGING UNIT

FIELD OF THE INVENTION

The present invention relates to the editing of digital radiographic images and more particularly to the automated deferred editing of such images.

BACKGROUND OF THE INVENTION

The field of medical radiography has undergone profound changes in the past few years. In particular, the development of new types of recording media using photoluminescent memory plates, well known by the name of "phosphor plates", has enabled digital medical imaging to be developed. Traditionally, radiographic images were obtained on photosensitive plates which, after processing in photographic processing baths, enable the radiographic image to be displayed. Technological developments in the past few years with regard to image processing have made it possible to envisage obtaining radiographic images which can be exploited from digital data.

A digital medical imaging unit is associated with a radiography system using "phosphor cartridges", that is to say cartridges provided with photoluminescent memory plates used to form a latent analog radiographic image.

In order to be able to exploit the latent image contained in the photoluminescent memory plate, the cartridge is inserted into a reading device in which the plate is extracted form the cartridge and then scanned with a reading beam so as to excite the plate locally. This excitation causes a light emission which is a function of the irradiation previously received by the plate. By means of a photosensitive sensor, the reading device converts the intensity of the radiation emitted by the plate into an analog electrical signal which is then converted into digital data. By scanning the plate, the reading device therefore supplies, for each plate, a digital representation of the information carried by the photoluminescent memory plate. The reading device is very often associated with an automatic cartridge dispenser enabling a plurality of cartridges to be disposed at the entry to the reading device. After the processing of a cartridge by the reading device, the latter erases any residual information on the plate and returns the cartridge to the dispenser and takes therefrom a new cartridge in order to process it.

The digital representation coming from the reading device is then processed by a suitable digital processing unit provided with distinct processing algorithms dependent on the type of radiographic image recorded on the photoluminescent memory plate. To do this, information relating to the type of radiographic examination carried out with the cartridge concerned is supplied to the processing unit.

The medical imaging unit also comprises a workstation which, after receipt of the digital medical images, makes it possible to edit the various images contained in the memory of the processing unit.

A description will now be given of the conventional use of a digital medical imaging unit. When it is desired to carry out a radiographic examination of a patient by means of a digital medical imaging unit, the information required for the identification of the patient is first of all introduced into the computer. In general the surname of the patient and his first name are introduced, sometimes his sex and his age. A unique identification number, which can be coded and printed in the form of a bar code on labels, is made to correspond to this information. Normally, each phosphor cartridge is identified unequivocally in order to be able to be recognized by the processing unit. In one particularly advantageous embodiment, the cartridges are identified by means of a bar code. During the radiographic examinations the type of examination recorded in each cartridge is introduced into the processing unit so as to obtain processed digital images whose visual presentation is close to the presentation obtained with silver halide radiographic plates. It is obvious that, when other universal types of processing are available, it will be possible optionally to dispense with such processing. Advantageously, in some medical imaging units, this information can be introduced into the processing unit by means of a bar code reader, preferably portable, which will capture the information directly at the time of the radiographic examination. In this way any possible mixing up of the cartridges is avoided when the examination requires more than one cartridge for the patient.

SUMMARY OF THE INVENTION

In a particularly advantageous known embodiment, at the time of exposure to X-rays, there are entered with a bar code reader, preferably portable, the code of the patient, the code of the cartridge, the type of examination or part of the patient observed (cranium, thorax, shoulder, hand, etc), the type of projection (profile, antero-posterior or AP, postero-anterior or PA), the orientation (landscape, portrait) with a view to the correct display on the screen or at the time of editing and optionally the position of the patient (lying down, standing, semiseated), the name of the person carrying out the examination and the technical data (kV, mAS, distance). Once the data have been entered, a validation data item or End is sent to the processing unit.

After the exposure of the cartridges to X-rays and the recording, in the processing unit, of the data relating to the examinations, the cartridges are inserted in the automatic dispenser associated with the reading device so as to obtain a digital representation of each of the radiographic images recorded in each of the cartridges.

By means of the information entered relating to each exposure, the processing unit applies the appropriate processing algorithms to the digital information and associates a specific patient with each of the cartridges.

Then, using a workstation, an operator is able to edit, on an editing medium, one after the other, the various images contained in the processing unit. In an automatic operating mode of the workstation, the printer produces one image from the processing unit per page of the editing medium as the processing unit delivers a processed digital image. Advantageously, provision can be made for the dimension of the editing medium to be determined by default either by the size of the cartridge or by the type of examination.

It has been proposed to group together several radiographs on a single editing page either manually or automatically as described in French patent application 96 01510 filed on Feb. 3, 1997.

In automatic editing mode, the order of introducing the cartridges into the reading device is important. This is because this order controls the response of the editing unit.

The present invention aims to provide a digital medical imaging unit which offers fewer constraints in the introduction of the cartridges into the reading device.

These and other aspects, objects, features and advantages of the present invention will be more clearly understood and appreciated from a review of the following detailed description of the preferred embodiments and appended claims, and by reference to the accompanying drawings.

DETAILED DESCRIPTION OF THE INVENTION

Figure 1:
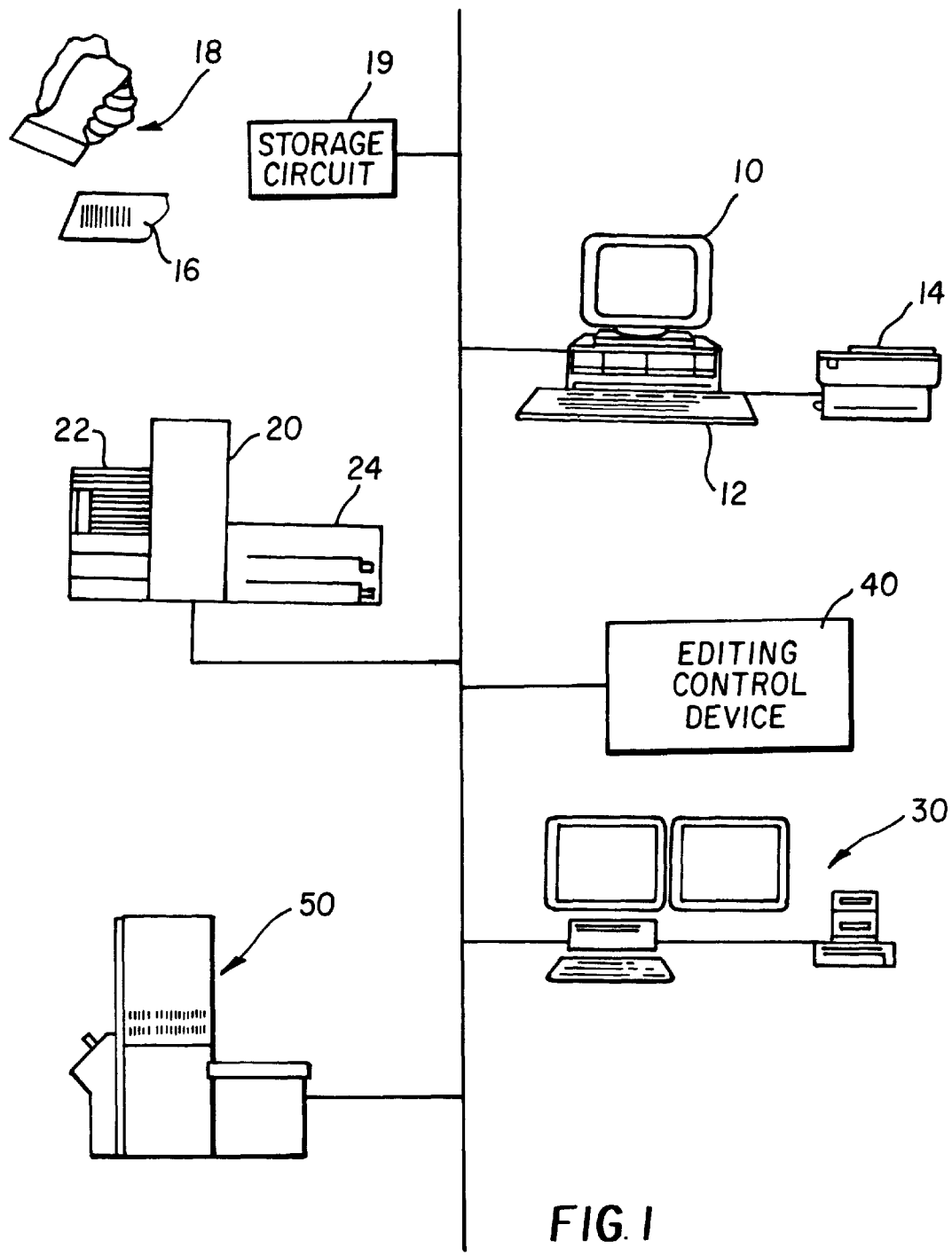
FIG. 1 depicts diagrammatically a possible architecture for a medical imaging unit.

FIG. 1 depicts diagrammatically the elements of a medical digital imaging unit and more particularly the logic connections necessary to such a unit. A digital medical imaging laboratory comprises, in addition to the apparatus for exposing the media for recording the radiographic image, a digital medical imaging unit. In such laboratories, the recording media consist of photoluminescent memory plates disposed in cartridges. As in traditional radiography, there are several plate formats and several cartridge formats.

As can be seen in FIG. 1, the medical imaging unit comprises an entry station 10, for example a personal computer, provided with a keyboard 12 and a printer 14 advantageously making it possible to edit information in the form of bar codes. The entry station 10 is used at the start of an examination to introduce the data relating to the patient and necessary for an interpretation of the images which will be edited. These data generally comprise the identity of the patient: his surname and first name and optionally his age or date of birth, his sex or other information. A unique code is associated with the data relating to the patient so as to cause each image to correspond unequivocally to a single patient (even when there are patients having identical surnames and first names). Advantageously, the code associated with the patient is converted into a bar code 16 which can be read by means of a data capture device 18 such as for example a bar code reader, known commercially. The reader 18 transmits the information contained in the bar code to a storage circuit 19 so as to be able to be used subsequently by the other components of the digital medical imaging unit.

The digital medical imaging unit also comprises a device 20 for reading the recording media on which a radiographic image of the patient has been formed. This device, known per se, can be the one sold under the commercial name "Kodak Digital Science Model 400 Digital Radiology System with Photoluminescent Screens" by the Eastman Kodak Company or any other equivalent device. Advantageously, the reading device 20 can be associated with an automatic feed dispenser 22 in which up to around ten cartridges, which will be processed successively by the reading device 20, can be inserted simultaneously. As is well known, the reading device is provided with a light source of the laser type, a scanning device enabling the laser beam to be moved along the photoluminescent plate which has been exposed to X-rays and a photosensitive detector for receiving the radiation emitted by the plate under the effect of the excitation supplied by this laser beam. The reading device 20 is associated with a processing unit 24 which comprises various image processing algorithms in order to improve the digital image supplied by the photosensitive detector. Each type of examination being associated with a given algorithm, it is necessary to associate, before the reading of a plate, the plate and the type of examination which has been recorded on this plate. Advantageously, this association is possible by virtue of the information transmitted to the circuit 19 for example by the bar code reader 18, preferably portable. Such a bar code reader makes it possible to enter, at the time of examination, the data necessary to the processing unit in order to provide a correct digital medical image. Advantageously, as is known, the bar codes representing the information to be entered comprise in their coding the type of information which they represent. For example, the codes relating to patients are preceded by the letter P, the codes for the cartridges are preceded by the letter C, the codes relating to the examinations are preceded by the letter E, etc. In this way, it is possible to enter the information in any order. In addition, if it is desired to modify an item of information, the entry of a new item of information of the same type automatically replaces the previous entry.

The digital medical imaging unit also comprises an editing station 30 provided with at least one display screen, a keyboard and optionally a mouse. This workstation transmits the images to be edited to a laser printer 50. Such an editing station is known commercially. It is offered by the company Kodak-Pathé® under the name MasterPage® workstation. Obviously any other similar device may be used. The editing station makes it possible, by means of suitable software, to associate several images on the same page of an editing medium contained in the printer 50, and to print them with this printer. In the preferred embodiment used with the invention, the printer is sold by Eastman Kodak Company under the trade name "Kodak Ektascan 2180 Laser Imager" and the editing medium is a black and white film of the Kodak Ektascan® type.

According to the invention, the processing unit 24 is also provided with an automatic editing control device 40. This control device, which can be in the form of a program, makes it possible to provide the editing station 30 with the information for automatically editing the images relating to a patient. The automatic editing control device 40 uses the information transmitted by the circuit 19 and relating to editing.

The information necessary to the editing station comprise first of all an indication relating to the editing medium format, which is chosen from amongst the three formats provided for the laser printer 50, for example 35×43, 20×25 or 28×35, and then information relating to an editing template or box chosen from amongst a template set. Obviously the types of template are designed and programmed according to the examinations most often used in the medical imaging laboratory.

After entering the usual information, the information relating to the size of the editing medium to be used is entered with the bar code reader. Then, before the insertion of each cartridge into the reading device, information of a first type for associating a specific patient with a cartridge and information of a second type relating to editing are entered.

In a specific embodiment, the storage circuit 19 forms an integral part of the reading device 20. This is the case with the device mentioned above and called the "Kodak Digital Science Model 400 Digital Radiology System with Photoluminescent Screens" from Eastman Kodak Company. In this specific embodiment, the editing control device 40 forms an integral part of the MasterPage workstation. However, it is clear that it is possible to design another type of installation in which the storage circuit 19 is independent of the reading device 20 and transmits the information to the reading device 20 at the moment when the latter identifies a cartridge in the course of scanning or processing and to the editing control device 40, which is completely independent, at the moment when a digital image is supplied by the reading device 20.

The digital image supplied by the reading device 20, which in reality is in the form of a digital file, comprises the image proper associated with a header in which are found the information entered by the bar code reader and an item of information relating to the time of exposure of the cartridge. In the header there is not only the information entered comprising notably the orientation of the image (portrait or landscape), the time when the information was entered, the format of the editing medium (35×43, 20×25, 28×35) and the number of radiographic images to be edited on one and the same page of the editing medium.

For a better understanding of the description which follows, the logic used by the device according to the invention will be described succinctly. Because of the difficulty of keeping the correct order of the cartridges when the reading device is loaded, it was determined that each series of images to be disposed on the same single page of an editing medium should begin with a cartridge for which the number of images to be edited has been captured and that the cartridges in a series should not be mixed with the cartridges of another series for one and the same patient.

Each time a digital image is received, coming from the reading device, the automatic editing control device adds the last image received to a list of the images to be edited, relating to a given patient. The automatic editing control device classifies this list chronologically, by means of an item of information contained in the header relating to the time at which the information concerning the examination which is contained in the cartridge was captured in the digital medical imaging unit or any other item of information enabling this chronological classification. Next, the automatic editing control device determines the number of images which must be associated with this last image received as well as the first image in the series. Then the automatic editing control device determines whether all the images in the series, to be printed on the same page of the editing medium, have been acquired by the reading device, in which case the editing can be performed. The images thus edited are then erased from the list of images to be edited.

The term "series of images" as used in the present application corresponds to the set of images to be edited on the same page of an editing medium.

At the moment when the digital medical imaging unit is started up, all the temporary recording areas are set to zero. Each time a digital image file, coming from the reading device 20, is received at 58, the automatic editing control device 40 adds the last image received to a list of the images to be edited relating to a given patient. It is obvious that, if the image received relates to a patient who is unknown to the digital medical imaging unit, the automatic editing control device 40 creates a new list relating to this patient. Once this list is updated, the automatic editing control device 40 chronologically orders, at step 159, the images relating to a patient, basing this on an item of information contained in the header of the file received. At this step, the automatic editing control device 40 keeps, for example by means of a pointer, the trace of the last image received.

Once this operation has been performed, the automatic editing control device 40 determines to which series of images this last image received belongs. In other words, the automatic editing control device 40 determines the number of images which must be associated with the last one in order to be edited in common on the same page of the editing medium. As indicated previously, the number of images in a given series to be edited on the same page of the editing medium has been captured, at least during the exposure of the first image in the series. To do this, the automatic editing control device 40 seeks, in an area TH of the header, the number $D_{image(n)}$ of images to be edited on the same page of the editing medium.

As indicated in the application cited previously, this number, because of problems of memory space, can be disposed in an existing area TH of the header normally containing another item of information of a different identifiable type; for example an item of alphabetic information compared with an item of numerical information, an item of numerical information lower than a normal minimum value contained in the area, an item of information preceded by a specific check character, or any other type of distinction. In the particular case, the information is a numerical value lower than a given value M. The automatic editing control device 40 therefore comprises a test (not shown) for verifying that the information contained in the area TH does indeed correspond to the required number of images per page of the editing medium. In the description which follows, when the area TH does not contain any information relating to editing, this state will be designated by an area TH containing a nil value.

Figure 2A:
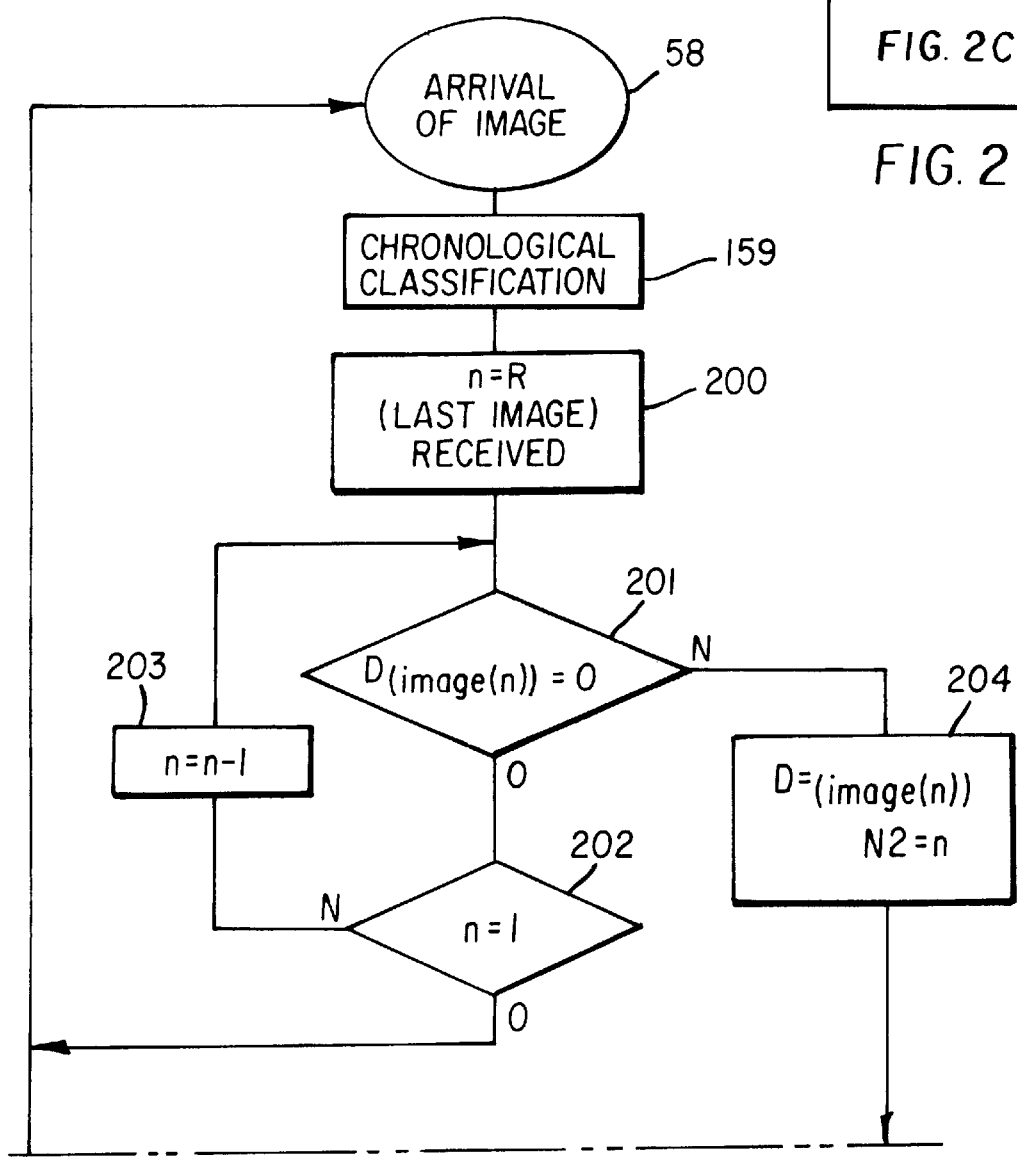
FIG. 2 depicts diagrammatically a flow diagram for the functions used by the device according to the invention.
Figure 3A:
FIGS. 3A and 3B are examples illustrating a series of information which can be provided by the device according to the invention and which will permit a better understanding of the explanations provided subsequently.

When the area TH contains an item of information D relating to the number of images to be edited on the same page of the editing medium, it will be considered that it belongs to a series D of D images, a series associated with this same number of images. When the area TH contains a nil value, the associated image belongs to a series of images D' whose number is determined by the first preceding image, in the chronologically ordered list, having in the area TH of its header a non-nil value. If no preceding image has any information relating to editing in the corresponding area TH, the image will not be edited. FIG. 3A is an example of values $D_{image(n)}$ of the various areas TH in a list of images to be edited and relating to a given patient; the character shown in bold represents the value $D_{image(n)}$ corresponding to the last image received and n represents the serial number of the corresponding image in the ordered list relating to a given patient. In the embodiment depicted in FIG. 2A, steps 200 to 204 make it possible to determine the type of series to which the last image received belongs.

First of all the automatic editing control device 40 determines the rank $R_{image(n)}$ of the last image received, in the example in FIG. 3A the value of $R_{image(n)}$ is 9. This value of $R_{image(n)}$ is introduced into a loop control area n which comprises steps 201 to 204. In the first step 201, the value $D_{image(n)}$ of the area TH of the header of the image of rank n is tested in order to determine whether the operator has captured an item of information relating to editing (according to the convention expressed previously, it is verified that the area is nil). If no editing information has been captured the reply is yes. In this case it is verified whether the image tested is the first image in the list, in which case it is not possible to determine the image number in the series and step 58 is returned to whilst awaiting the receipt of a new image. If the image is not the first image in the series, the value controlling the loop is decremented at 203 and step 201 is returned to in order to test the value $D_{image(n)}$ contained in the area TH of the image of rank n−1. When this value is non-nil, it is the first image in the ordered list which precedes the last image received and whose value $D_{image(n)}$ is different from zero. The processing carried out at step 201 continues then with step 204 in which the value of $D_{image(n)}$ is saved in an area D and the rank $R_{image(n)}$ of the corresponding image is saved in an area N2.

After having determined the number of images to be printed on the same page of the editing medium as the last image received, that is to say after step 204, the processing continues, as depicted by the arrow A, so as to determine the first cartridge in the series.

The first image in the series corresponding to the last image received has the same value $D_{image(n)}$ as the image of rank N2 and is separated from this cartridge only by cartridges having, as the value of $D_{image(n)}$, either zero or a value of $D_{image(n)}$ identical to the image N2, that is to say D. Steps 210 to 217 define a loop for detecting the first image in the series. Because each series begins with an image where the number of images in the series has been captured in the area TH of the header, when an image having a value $D_{image(n)}$ different from the value corresponding to the image N2 is encountered, this will mean that the start of the series has been passed.

Figure 2B:
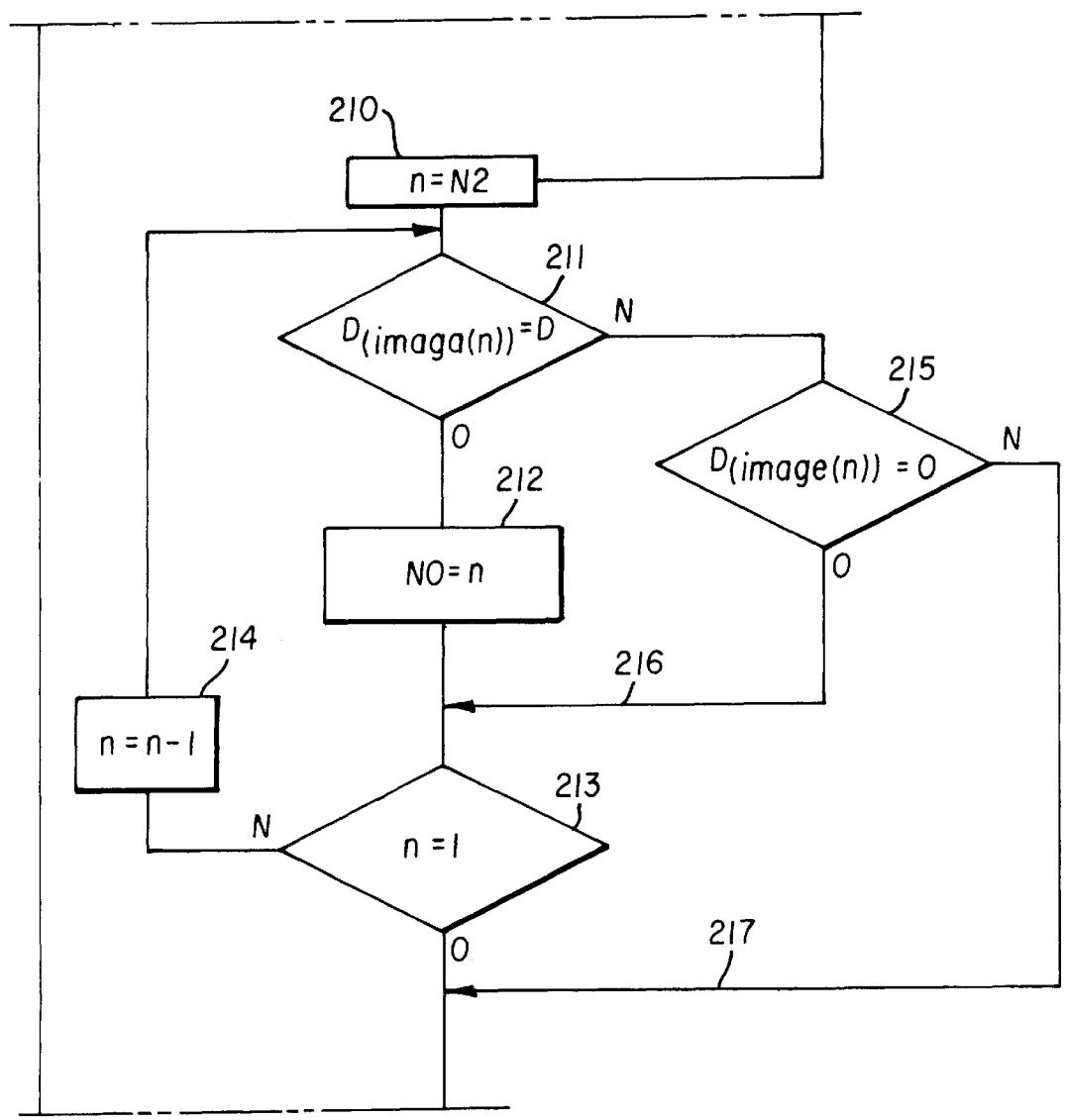

At step 210, the loop value n recorded in a control area is initialized to the value N2. In the first step 211, a test is carried out of the value $D_{image(n)}$ of the area TH of the header of the image of rank n with respect to D, corresponding to the value $D_{image(n)}$ of the image of rank N2 ($D_{image(N2)}$=D). If the test 211 is true, which is always the case the first time the processing reaches this step after the receipt of a new image at 58, the value n corresponding to the rank of the image whose header is examined is recorded at 212 in an area N0. This value corresponds to the first image in the series. After having recorded this value, it is verified at 213 whether the image tested is the first image in the list, in which case the following step is passed to, represented by the arrow B, where the rank of the last image in the list to be edited with the last image received is determined. If the image is not the first image in the series, the value n controlling the loop is decremented at 214 and step 211 is returned to in order to test the value $D_{image(n)}$ contained in the area TH of the image of the rank which has become n−1. When the value $D_{image(n)}$ is different from D, it is tested at 215 whether this value is nil, in which case the image tested may belong to the series D (if another cartridge having this value D precedes the one tested). However, this image is not the first image in the series since its value $D_{image(n)}$ is nil. In this case, the processing is returned to step 213 via the path 216 in order to verify the existence of a prior image in the series without updating, at step 212, the value of the area N0 corresponding to the first image in the series. The processing continues as indicated previously and depicted schematically in FIG. 2B. When the value of $D_{image(n)}$ tested at 215 is not nil, this image does not correspond to the same image as the last image received and the processing has therefore determined what was the rank of the first image in the series corresponding to the last image received. The processing is therefore continued, by virtue of the path 217, with the following step indicated previously and represented diagrammatically by the arrow B.

Having determined the number of images contained in the series associated with the last image received and having determined the first image in the series, the automatic editing control device 40 can then determine whether all the images in the series have been processed. The last image in the series to be edited in the current list of the images relating to the given patient is therefore determined. The maximum serial number of this image is the value $R_{image(n)}$=N0+D−1; none of the images between N0 and N0+D−1 must contain, in their respective area TH, any box value $D_{image(n)}$ different from zero or from D. The automatic editing control device 40 checks that all the images to be edited are present by means of steps 220 to 227. As will be noted, N0+D−1 is greater than or equal to N2 and it has already been checked that the images between N0 and N2 do not have any value $D_{image(n)}$ different from zero or from D. The automatic editing control device 40 takes these advantages into account in order to increase the response speed.

Figure 2C:
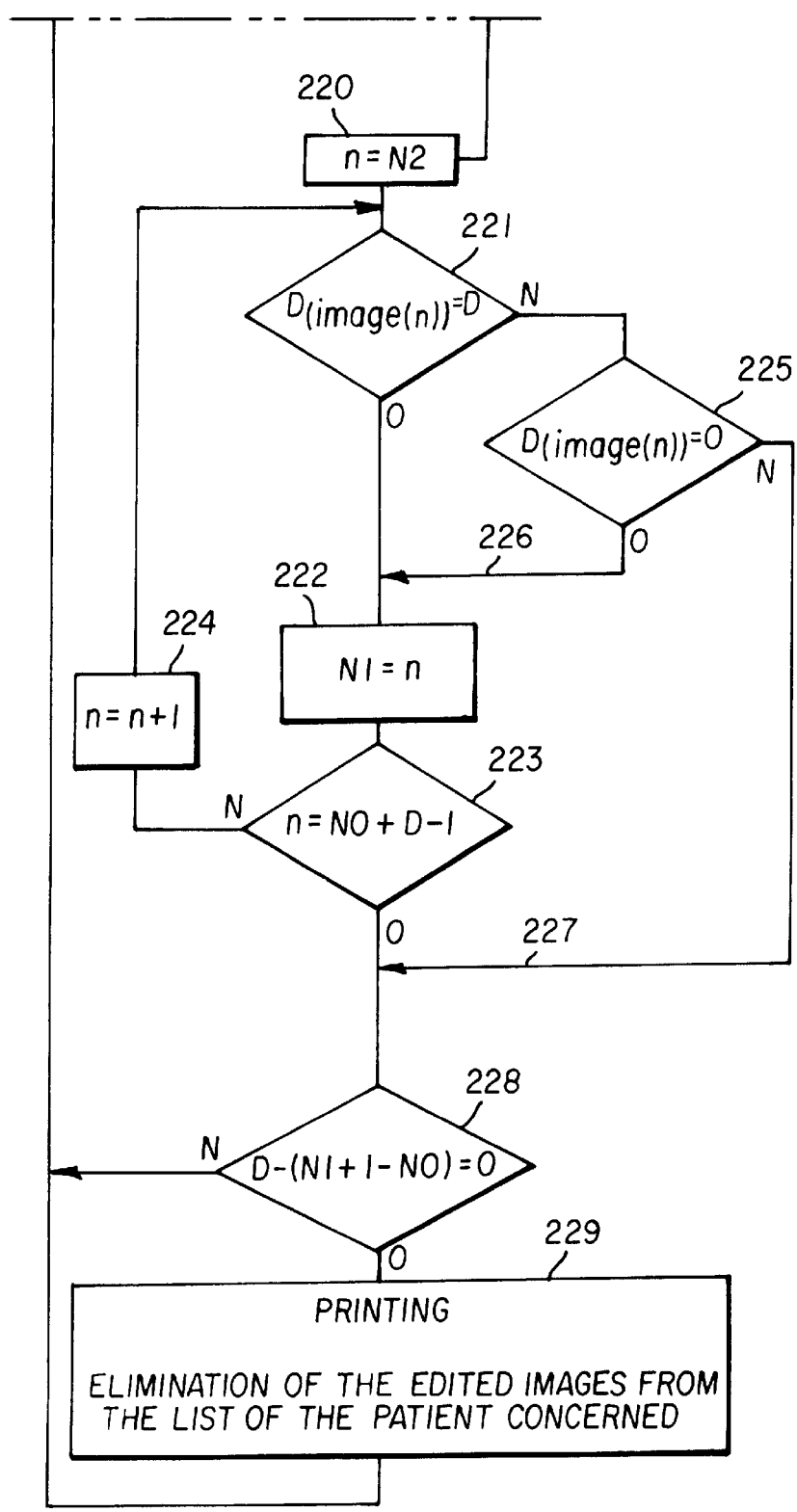

At step 220, the loop value n recorded in a control area is initialized to the value N2. In the first step 211, a test is carried out of the value $D_{image(n)}$ of the area TH of the header of the image of rank n with respect to D, corresponding to the value $D_{image(n)}$ of the images in the series. If the test 221 is true, which is always the case the first time the processing reaches this step after the reception of a new image at 58, the value n corresponding to the rank of the image whose header is examined is recorded at 222 in an area N1. This value is considered to correspond to the last image in the series. After having recorded this value, it is verified at 223 whether the image tested is indeed the last image in the list whose rank is equal to N0+D−1, in which case the following step 228 is passed to, which will be described subsequently. If the image is not the last image in the series, the value n controlling the loop is decremented at 224 and step 221 is returned to in order to test the value $D_{image(n)}$ contained in the area TH of the image of the rank which has become n−1. When the value $D_{image(n)}$ is different from D, the test 221 sends the processing to 225, where it is tested whether this value of $D_{image(n)}$ is nil, in which case the image tested may belong to the series D. In this case, the processing is sent to step 223 via the path 226 in order to record the new value of the rank of the last image tested and then, as indicated previously, it is checked at 223 whether the rank corresponds to the rank of the last image to be edited. The processing continues as indicated and depicted schematically in FIG. 2C. When the value of $D_{image(n)}$ tested at 225 is not nil, this image does not correspond to the same series of images as the last image received since $D_{image(n)}$ is also different from D and the automatic editing control device 40 has therefore determined what was the rank of the last image in the series corresponding to the last image received. The processing is therefore continued, by virtue of the path 227, with the following step 228 indicated previously.

At 228 it is verified that the number of images contained between the image considered to be the first image in the series (image of rank N0) and the image considered to be the last image in the series (image of rank N1) is indeed equal to D, that is to say to the number of images to be associated on the same page of the editing medium. When all the images have not been digitized by the reading device, the processing is sent back to 58 whilst awaiting a new image. When the automatic editing control device 40 determines that all the images have been digitized, the processing passes to step 229, in which the editing of the images is demanded. When the editing has been demanded, the edited images are eliminated from the list. As can be seen in the example in FIG. 3A, the list then takes the form of FIG. 3B.

Obviously modifications can be made whilst keeping the logic used by the invention. For example, instead of storing the time at which the information of the first type was captured, the system can store a different chronological index such as for example a serial number which is incremented with each item of information of the first type associated with a cartridge, and the chronological classification is no longer based on the time but on an item of information fulfilling the same role.

Figure 3B:

As can be remarked from FIG. 3B, if p is equal to 4 and x also, the images of rank 4, 5 and 6 could possibly belong to the same series, which cannot be the case since the series are in principle taken chronologically without interruption, the cartridge of rank 6 does not belong to the series p. If the next cartridge received belongs to the series p, because of the construction of the system the images of rank 4, of rank 5 and of rank 6 in FIG. 3B will be edited on the same page of an editing medium with the last image received, which is erroneous. It can be seen therefore that a system is needed which provides still less constraint on the order of introducing the cartridges into the reading device.

In another embodiment in which it is desired to limit even more the constraints relating to the order of introducing the cartridges into the reading device, the information of the second type comprises not only the number of images to be edited on the same page of the editing medium but also an item of information relating to the series of images. For example, this information can be the number of the series. In this case two successive series of x images relating to the same patient will bear information (x,1 and x,2) which can be distinguished. The series of images will be more easily separated. It is possible either to capture the information manually at each radiograph, or to use an "intelligent" capture device. It suffices to make provision for the capture device automatically to take forward, for all the images in the series, the number of the series and the number of images in this series. It may be advantageous for the device to have a memory which is automatically incremented at each new series, a "new series" of images button being provided to supply the information to the capture device. This arrangement thus makes it possible to separate the images of different series and the only remaining constraint is to produce and/or identify the images in a series without stopping to make another series.

For other applications, it may be advantageous to provide for the editing of images having compatible boxes, that is to say either the same value of $D_{image(n)}$ or a nil value, being adjacent after the elimination of certain images from the list relating to a patient. It suffices to do this to determine, as the last image received, one of the images which was situated alongside the list which has just been eliminated and to resume processing at step 159. In the example depicted in FIGS. 3A and 3B, after editing the list and eliminating the images from this list, the processing chooses the image whose serial number is 6 and which has, as the value of $D_{image(n)}$, the value x as the last image received, and then resumes at step 159. Obviously it is also possible to choose, as the last image received, the image whose serial number is 5. In this case, if p and x are equal to 3, these three images are edited on the same page of an editing medium. It is also clear that other images can be chosen optionally in a random fashion.

The invention has been described with reference to a preferred embodiment. However, it will be appreciated that variations and modifications can be effected by a person of ordinary skill in the art without departing from the scope of the invention.

What is claimed is:

1. In a method for the automatic editing of a plurality of digital images on the same page of an editing medium by means of a digital medical imaging unit comprising first media on each of which a latent radiographic image is recorded and:

a) a capture means for codifying information relating to a patient for whom digital radiographic images are to be produced, b) a device for reading each first recording medium so as to obtain a digital representation of the radiographic image carried by the first recording medium, c) a device for identifying each first successive recording medium introduced into the reading device, d) an editing means designed to reproduce, on an editing medium, at least one digital image processed by the processing unit, and in which:

1) the information relating to the patient are codified unequivocally, 2) the radiographic image recorded on a first recording medium is digitized by means of the reading device, 3) each first recording medium is associated unequivocally with a given patient before the digitizing of the images and by capturing an item of information of a first type, 4) the digital representation of this radiographic image is transmitted to the editing means, and 5) the digital image is edited on the editing medium, improvement comprising the steps of:

capturing, before the digitizing of the image recorded on the first medium, an item of editing information of a second type controlling the editing means is captured so as to edit automatically on the same page of an editing medium determined number of digital radiographic images, associating with the capture of the information of the first type an item of chronological information making it possible to determine subsequently the order in which the images have been captured, classifying, per patient in the chronological order of capture of the information of the first type, the digital images each time a digital image supplied by the reading device is received, determining to which series of images this received image belongs, and verifying that the series of images associated with the image received is complete, and then editing the plurality of digital images on the same page of the editing medium.

2. Method according to claim 1, in which the capture of the information of the first type consists of capturing the identification of the patient.

3. Method according to claim 1, in which the capture of the chronological information consists of capturing the time at which the information of the first type was captured.

4. Method according to claim 1, in which the capture of the information of the second type consists of capturing, at least at the time of the capture of the first medium of the series, the number of images to be associated on the same page of the editing medium.

5. Method according to claim 1, in which the capture of the information of the second type consists of capturing, at the time of capture of each of the first media in the series, the number of images to be associated on the same page of the editing medium.

6. Method according to claim 4, in which the capture of the information of the second type also contains a specific item of information of each series.

* * * * *